United States Patent
Hamid (10) Patent No.: US 7,833,732 B2
(45) Date of Patent: Nov. 16, 2010

(54) ACUTE RENAL INJURY

(75) Inventor: Rabb Hamid, Ellicott City, MD (US)

(73) Assignee: The John Hopkins University, Baltimore, MD (US)

( * ) Notice: Subject to any disclaimer, the term of this patent is extended or adjusted under 35 U.S.C. 154(b) by 290 days.

(21) Appl. No.: 11/995,961

(22) PCT Filed: Jul. 20, 2006

(86) PCT No.: PCT/US2006/028032
§ 371 (c)(1), (2), (4) Date: Jul. 11, 2008

(87) PCT Pub. No.: WO2007/013919
PCT Pub. Date: Feb. 5, 2007

(65) Prior Publication Data
US 2009/0220526 A1     Sep. 3, 2009

Related U.S. Application Data

(60) Provisional application No. 60/701,441, filed on Jul. 21, 2005.

(51) Int. Cl.
*G01N 33/53* (2006.01)
*G01N 33/543* (2006.01)

(52) U.S. Cl. ............... 435/7.21; 435/7.1; 436/501; 436/518; 422/50; 422/60; 424/9.1

(58) Field of Classification Search ............... None
See application file for complete search history.

(56) References Cited
FOREIGN PATENT DOCUMENTS
WO        03/082258 A       10/2003

OTHER PUBLICATIONS

Zernecke, A. et al., "Combinatorial model of chemokine involvement in glomerular monocyte recruitment: Role of CXC chemokine receptor 2 in infiltration during nephrotoxic nephritis", J. Immunol. 2001, vol. 166, pp. 5755-5762.

Huber, T.B. et al., "Expression of functional CCR and CXCR chemokine receptors in podocytes", J. Immunol. 2002, vol. 168 pp. 6244-6252.

Molls et al., "Keratinocyte-Derived Chemokine is an Early Biomarker of Ischemic Acute Kidney Injury," American Journal of Physiology-Renal physiology, 2006, vol. 290, No. 5, pp. F1187-F1193.

Miura et al., "Neutralization of 1-3, 5-13 Groalpha and Macrophage Inflammatory Protein-2 Attenuates Renal Ischemia/Reprefusion Injury," American Journal of Pathology, 2001, vol. 159, No. 6, pp. 2137-2145.

Leonard et al., ""15-EPI-16-(Para-Fluorophenoxyl)-Lipoxin A4-Methyl Ester, a Synthetic Analogue of 15-EPI-Lipoxin A4, is Protective in Experimental Ischemic Acute Renal Failure," Journal of the American Society of Nephrology, 2002, vol. 13, No. 6, pp. 1657-1662.

*Primary Examiner*—Lisa V Cook
(74) *Attorney, Agent, or Firm*—Banner & Witcoff, Ltd.

(57) ABSTRACT

We disclose a new and useful biomarker for acute kidney injury (i.e., AKI), renal ischemia reperfusion injury (i.e., IRI), ischemic acute kidney injury, and/or ischemic acute tubular necrosis (i.e., ATN). The biomarker is GRO-alpha (i.e., CXCL1, chemokine C-X-C ligand 1, GRO1, GROa, MGSA, MGSA alpha, MGSA-a, NAP-3, SCYB1). We detected the biomarker using a QUANTIKINE® human GRO-alpha immunoassay (Cat. No. DGR00, R & D Systems, Minneapolis, Minn.). In addition, we disclose a method of treating lung damage.

51 Claims, 8 Drawing Sheets

ACUTE RENAL INJURY

This application claims the benefit of provisional application Ser. No. 60/701,441 filed Jul. 21, 2005, the disclosure of which is expressly incorporated herein.

This invention was made using funds from the U.S. government. Under the terms of grants P50HL073994 and DK54770, from the NHLBI and the NIDDK, respectively, the U.S. government retains certain rights in the invention.

TECHNICAL FIELD OF THE INVENTION

This invention is related to the area of diagnostic, prognostic, and stratifying procedures. In particular, it relates to the detection of an early marker of kidney injury and increased risk of morbidity and mortality.

BACKGROUND OF THE INVENTION

Acute renal failure (ARF), also recently known as acute kidney injury (AKI), is a syndrome with high mortality and morbidity, for which there is no specific therapy except supportive care (5; 17). There is an urgent need to develop effective therapeutics for ARF. Histologically, ischemic ARF is characterized by acute tubular necrosis, however a major limitation in approaching the disease is the lack of clinically feasible diagnostics for early detection of ischemic ARF, such as the use of serum troponin and creatine phosphokinase (CPK) for myocardial ischemia reperfusion injury (IRI) (4). Recent studies have identified proteins including KIM-1, lipocalin, IL-18, NHE3, actin, and retinol binding protein among others as potential biomarker candidates in ischemic ARF (13). However, none of them have been fully validated or are in routine clinical use. There remains a strong need for discovery and validation of additional candidate markers, in particular for early detection (1).

SUMMARY OF THE INVENTION

According to one embodiment of the invention, a method is provided for detecting acute kidney injury (AKI). A first amount of Gro-alpha is determined in a sample from a human patient. The sample may be urine, serum, or tissue. The determined first amount for the patient is compared to a second amount determined for control patients with healthy kidneys. If the first amount is elevated relative to the second amount determined for control patients, then the patient is assigned to a first group. And if the first amount is not elevated relative to the second group then the patient is assigned to a second group. The first group is identified as having AKI.

In an alternative embodiment, the amount of Gro-alpha is determined by measuring mRNA encoding Gro-alpha.

In another alternative embodiment, when the patient is assigned to the first group one predicts that the patient will need dialysis.

In another alternative embodiment, when the patient is assigned to the first group one recommends dialysis for the patient.

In another alternative embodiment, patients assigned to the two groups are compared for efficacy of drugs or other therapeutic regimens.

In another alternative embodiment, one prescribes a drug or therapy if the patient is assigned to the first group.

In another alternative embodiment, if a patient is assigned to the first group one predicts a higher risk of morbidity and/or mortality.

According to another embodiment a method is provided for reducing lung damage associated with acute kidney injury. An antibody which specifically binds to human Gro-alpha is administered to a human patient suspected of having acute kidney injury. The risk of mortality is thereby reduced.

These and other embodiments which will be apparent to those of skill in the art upon reading the specification provide the art with methods for earlier diagnosis, prognosis, and treatment.

BRIEF DESCRIPTION OF THE DRAWINGS

FIGS. 2A-2H show very early and progressively worse histologic changes after renal IRI. Kidney sections from the mice underwent IRI or sham surgery and sacrificed at 1, 3, 24, and 72 h after surgery. FIG. 2A. 1 h sham; FIG. 2B. 1 h IRI: early red cell congestions, the cytoplasm of some tubular epithelial cells were condensed cytoplasm of select epithelial cells, slightly edematous endothelium; FIG. 2C. 3 h sham; FIG. 2D. 3 h IRI: significant congestion with erythrocytes sludged in capillaries, cytoplasm of the tubular epithelium condensed, limited epithelial cell necrosis, moderate cast formation, swollen endothelial cells and widened basal membrane. FIG. 2E. 24 h sham; FIG. 2F. 24 h IRI: Widespread tubular injury with extensive tubular necrosis and cast formation, markedly edematous endothelial cells, capillaries were filled with erythrocytes. FIG. 2G. 72 h sham; FIG. 2H. 72 h IRI: similar to 24 h description.

FIGS. 3A-3D show representative chemokine/cytokine expression in mouse kidney after IRI. Cytokines were measured with a protein multiple bioplex technique from mouse kidney tissue homogenates. Kidney samples were harvested at the designated intervals following surgery from normal mice (0 h—no surgery), and mice that underwent IRI or sham surgery (n=5 per group for each cytokine) for analysis using the multiplex protein assay: FIG. 3A: a significantly early increase at 3 hour after ischemia in KC, which persisted; FIG. 3B: trend towards increased TNF at 24 and 72 hrs; FIG. 3C: significant decrease in IFN-γ at 72 hr; FIG. 3D: significant increase in Mip-1a at 24 hr. (* or **, $P<0.05$ vs. sham groups).

FIG. 4A-4F show representative cytokine expression in mouse kidney after IRI. FIG. 4A: decreased IL-1α at 24 and 72 hr postischemia; FIG. 4B: decrease in IL-2 at 72 hr; FIG. 4C: trend to decrease in IL-4 with time; FIG. 4D: significant increase in IL-6 at 24 hr; FIG. 4E: increase in IL-12(p40) at 24 hr; FIG. 4F: trend to late increase in G-CSF at 24 and 72 hr. (* or **, $P<0.05$ vs. sham groups)

DETAILED DESCRIPTION OF THE INVENTION

The inventor has developed a means for early detection of acute kidney injury in humans. Expression and/or secretion levels of Gro-alpha have been found to increase immediately after injury. Such injury may be caused by an ischemic event, for example, caused by a malfunctioning transplanted kidney, by heart surgery, by contrast agent injection, by sepsis, by toxins, by shock, and by an episode of hypotension.

The amount of Gro-alpha can be measured in a tissue, in serum, or in urine. Other body fluids and samples may also be used including but not limited to blood, plasma, stool, bronchioalveolar lavage, sputum, saliva. Typically samples from test and control patients, i.e., sick and healthy patients, are drawn from the same type of tissue or fluid source and are prepared and tested in the same manner. Comparisons may be done on samples that are run side-by-side, or may be done to historical control samples or historical values. Statistical tests will determine whether an elevation is significant or not or whether a test value is outside of the range of the normal controls. Even if statistical significance is not achieved and a value is considered borderline or indeterminate, these data may be combined with other clinical or laboratory findings to achieve relevance. Additional samples taken at other time points may also be tested to determine relevance of a borderline or indeterminate value. Thus a rising or falling value may be interpreted or interpolated to arrive at a useful piece of information in diagnosing, prognosing, or treating the patient.

Elevated levels of Gro-alpha compared to healthy controls are used to assign the patient to a group. The group consists of persons identified as having acute kidney injury. Such an assignment may serve to provide a diagnosis, a prognosis, or a treatment regimen. The groups may be used in clinical trials to determine safety and/or efficacy of a drug or other treatment of patients stratified according to the Gro-alpha level.

Elevated levels may be defined differently according to the source of the samples and the method of preparing and assaying them. The elevated levels may be set at a level which is at least 2-, 3-, 4-, or 5-fold higher than the controls. The levels will be set based on statistical significance of the data set for each method and type of samples. If desired, levels of Gro-alpha can be normalized against amounts of creatinine which are assayed in the same samples. Other genes or proteins which can be used for normalization are those considered housekeeping genes, i.e., those whose expression and/or secretion is relatively stable independent of conditions.

Preferably the assays will be done early after a known or suspected bodily insult. For example cardiac surgery and renal transplant are suspected bodily insults. Early times are within 1, 3, 6, or 12 hours. The assays can be performed before an increase in creatinine is detectable in the serum or urine. Quick and early assays permit best treatments and practices to be applied to minimize or palliate renal damage. Tests can be done before an expected or planned insult, such as surgery, to determine if there is an increased likelihood of a bad outcome, whether morbidity or mortality. In some cases, in combination with other clinical indications and risk factors, a procedure may be avoided or delayed until the patient's condition can be stabilized or improved.

The amount of Gro-alpha protein can be measured using any technique known in the art, whether it involves direct detection of protein or mRNA encoding the protein. Commercial kits are available for assaying Gro-alpha and these can be used. RT-PCR can be used, for example, for assaying mRNA. cDNA or cRNA can be measured as a way to determine the amount of mRNA. Nucleic acids can be quantitated by an means known in the art, including but not limited to using a nucleotide array. Antibodies can be used to detect and quantitate the protein. These can be in solution or immobilized on a solid support. Antibodies can be monoclonal or polyclonal. They can be immobilized in an array on a solid support, or they can be, for example, on beads that are arrayed in a microtiter dish. The human Gro-alpha protein itself and the mRNA encoding it are well known in the art. The official symbol for the protein is CXCL1 and its official name is chemokine (C-X-C motif) ligand 1 (melanoma growth stimulating activity, alpha) [Homo sapiens]. Other alternative names used for this protein are GRO1, GROa, MGSA, MGSA alpha, MGSA-a, NAP-3, SCYB1, GRO1 oncogene (melanoma growth stimulating activity, alpha); GRO1 oncogene (melanoma growth-stimulating activity); chemokine (C-X-C motif) ligand 1; melanoma growth stimulatory activity alpha. The gene encoding the protein is found on human Chromosome 4 at locus 4q21. The protein has 107 amino acids and one particular sequence from one particular human can be found at NP_001502 of GenPept. One particular sequence from one particular human encoding the protein can be found at NM_001511 of GenBank. The primary translation product includes a signal peptide which is encoded by nucleotides 80 to 181 and the mature peptide is encoded by nucleotides 182 to 400. The coding sequence is located at nucleotides 80 to 403.

Some of the high mortality attributable to acute kidney injury results from distal organ damage. Thus, even when injured kidneys are dialyzed, a large number of patients die. One of the significantly damaged distal organs is the lung. To counteract an early spike in the amount of Gro-alpha in the lungs, antibodies specific for human Gro-alpha can be delivered, either systemically or directly to the lungs. Antibodies can be of any variety, whether polyclonal or monoclonal, human or humanized or from another animal, antibody fragments such as F(ab)2 or F(ab')$_2$ or single chain antibodies. They can be neutralizing antibodies. They will typically react with Gro-alpha and not to other proteins whether related or not. A typical antibody that is specific for Gro-alpha will react with the cognate antigen at least 2, at least 3, at least 5, at least 10 times more than to unrelated or related antigens. The antibodies can be administered in an aerosol via the nose. The antibodies can be instilled using an endobronchoscope. The antibodies can be injected intravenously. Early treatment is desirable to precede or coincide with a spike in lung Gro-alpha. Although applicants do not wish to be constrained by any particular theory or mechanism, it is believed that the chemokine is produced in the kidney and released to the lung.

Ischemic acute kidney injury remains a major diagnostic and therapeutic problem in native kidneys and allografts. A major barrier to clinical trials in renal IRI has been the late start of therapy, in part due to a lack of early biomarkers. We utilized a new protein array technique to identify potential pathophysiologic mediators of the inflammatory injury following renal IRI, and unexpectedly observed a very early rise in KC in kidney and blood, indicating that KC may be useful as an early biomarker for renal IRI. Preliminary studies translating this to humans demonstrated that the human analogue of KC, Gro-α, can be measured in urine early after kidney transplantation and correlates with increased early injury.

The crucial role of inflammation and the immune response in the pathogenesis of ischemic ARF is well-established, with many pro-inflammatory cytokines/chemokines being upregulated in the kidney at the protein or mRNA level after renal IRI (3; 8; 11; 15; 21). We therefore used a cytokine/chemokine protein array to analyze the protein expression patterns in postischemic murine kidney at early and later times after IRI. We observed a time-dependent increase in several potential mediators in the post-ischemic kidney, including KC, MIP-1α, IL-6, IL-1α, and IL-12 (p40). Of these, we focused on KC for several reasons. First, the marked upregulation of KC in ischemic kidney was relatively selective. Second the increase in KC preceded the changes seen for other potential mediators. Finally, the increase in KC occurred well before a rise in serum creatinine (SCr).

KC can be secreted in most organs by a variety of cells including neutrophils, epithelial cells, endothelial cells, smooth muscle cells, fibroblasts, macrophages, platelets and lymphocytes (19). The main stimuli for KC production identified to date are IL-1, TNF-α, bacterial products, radical oxygen species, and LPS, as well as the T cell products IL-4 and IFN-γ which are often present at the site of injury (19). One study found renal KC mRNA to be increased between 1-4 h after IRI (16). In another study kidney KC mRNA and protein levels peaked at 9 h post-ischemia in C57BL/6 mice after renal IRI, and antibodies to KC administered just prior to reperfusion produced a decrease in neutroplhil infiltration and lower serum creatinine compared to mice treated with control serum (11). Unilateral clamping of the left renal pedicle for 45 min in Swiss mice produced a peak in KC mRNA levels in left kidney at 6 h (2). Our findings are consistent with the results of those studies, but derived from a broader-based search for potential inflammatory mediators using the multiplex cytokine assay. Armed with this information, we hypothesized that KC protein could be a useful early biomarker following renal IRI. Using an ELISA technique, we found that serum KC was elevated as early as 1 h postischemia, and decreased to baseline by 24 h. Since the composition of urine can provide insights into pathophysiologic events in the kidney, and in humans can be non-invasively collected, we measured urine KC as a potential early indicator of acute kidney injury. KC was markedly increased in the urine by 3 h after IRI in mice. To extend this novel finding, we performed preliminary studies in humans to examine if these findings were translatable for potential diagnosis and prognosis of renal injury in patients. There was a significant increase in the human KC analogue, Gro-α, in the urine samples from deceased donor kidney transplant patients with delayed graft function requiring dialysis compared to those with prompt graft function or live donor kidney transplants, and this correlated with ischemic acute tubular necrosis (ATN) on biopsy. These findings indicate that urine Gro-α levels may be a useful biomarker for detection of significant ischemic ATN, thereby facilitating non-invasive identification of patients who are candidates for intervention trials for ischemic ARF. However, we recognize that early allograft injury is more complex than ischemia reperfusion alone, and reflects an interplay of additional immunologic and toxic factors.

There are a number of new potential biomarkers for AKI. Lipocalin has recently been showed to be highly sensitive of kidney injury in a recent study of children after cardiac bypass (10). KIM-1 has been shown to correlate closely with various forms of kidney injury, and may well be a pathogenic molecule in the development of ARF as well (6). IL-18 has shown increasing promise, as have other cytokines (7; 12). Urinary enzymes are also potentially valuable biomarkers (20). Despite the promise for clinical use of these markers, there is still an important need to develop and validate new markers of ARF. Gro-α measurements can be used in conjunction with any of the other biomarkers identified for AKI, sepsis, shock, toxic shock, etc.

Our current study focused on biomarker discovery and initial validation of KC and it's human analogue Gro-α. However, the mechanism of action of KC in the injury or repair process has not been fully worked out. Despite studies demonstrating a protective role of KC blockade (11), blocking KC has enhanced plaque formation in apoE deficient mice (9). Thus, KC appears to have multiple roles. In addition, immunodetection of KC in serum and urine may not correlate with function, and further studies including examining chemokinesis-inducing activity of KC in these fluids is required (18).

These data, starting with a protein array in mice, then validating with ELISA, followed by pilot studies in man, suggest that murine KC, as well as its human analogue Gro-α, is a novel early biomarker for ischemic acute kidney injury. Future studies specifically designed to test this in humans will be used to validate this. In addition to being a biomarker, KC/Gro-α may play a causative role in the pathophysiology of ischemic renal injury, and therefore is a potential target for novel therapies to treat this clinically important problem.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials And Methods

Animals

Male C57BL/6 mice were obtained from The Jackson Laboratory (Bar Harbor, Me.) and housed under pathogen-free conditions, according to NIH guidelines.

Surgical Procedures

An established model of renal IRI was used (14), and sterile techniques were followed at all times. Briefly, mice weighing 25-30 g were anesthetized with an i.p. injection of sodium pentobarbital (75 mg/kg). Bilateral flank incisions were made, and the kidneys were exposed. Following abdominal incisions, renal pedicles were bluntly dissected and a non-traumatic vascular clamp (Roboz microaneurysm clamp; Roboz Surgical Instruments, Washington, D.C.) was applied across each of the pedicles for 30 min. During the procedure, animals were kept well hydrated with warm saline and at a constant temperature (37° C.). After 30 min of ischemia, the clamps were removed, the wounds sutured, and the animals were allowed to recover with free access to food and water. Sham animals underwent similar surgical procedures without renal pedicle clamping. IRI and sham animals were sacrificed at 1, 3, 24, and 72 h after ischemia or sham surgery, using i.p. injection of sodium pentobarbital (150 mg/kg). Normal animals were also sacrificed at time 0.

Sample Harvesting and Collection

At sacrifice, mice were euthanized, 0.5 ml blood was collected from the inferior vena cava, and urine was collected by bladder puncture. Blood and urine were centrifuged to obtain serum and supernatant, respectively, and stored at −80° C. for ELISA. One kidney was snap frozen and stored at −80° C. The other kidney was stored in formalin for histology.

Pathological Evaluation of Post-Ischemic Kidneys

At sacrifice, one kidney from each mouse was dissected and cut coronally. These sections were fixed in 10% formalin and processed for histology using standard techniques as previously described (14).

Renal Function

Blood samples were obtained at sacrifice from all mice at various time points, and serum creatinine (SCr) levels were measured as a marker of renal function, using a 557A Creatinine kit (Sigma Diagnostics, St. Louis, Mo.) and analyzed on a Cobas Mira S Plus automated analyzer (Roche Diagnostics Corp. Indianapolis, Ind.).

Protein Array for Cytokines in Kidney Tissue from Mice

Total Protein Analysis

Kidney samples were thawed over ice. Part of each kidney was homogenized in T-PER Tissue Protein Extraction Reagent (Pierce, Rockford, Ill.). The homogenate was centrifuged at 10,000 rpm for 5 min at 4° C. The supernatant was collected to determine total protein concentration using a micro BCA protein assay kit (Pierce, Rockford, Ill.). From the remaining kidney, tissue samples containing 500 µg/ml protein per sample were then weighed out and used for cytokine analysis.

Cytokine Analysis

Weighed kidney samples containing 500 µg/ml protein per sample were homogenized with cell lysis buffer (Cell Lysis Kit, Bio-Rad Laboratories Inc., Hercules, Calif.). Tissue homogenates were centrifuged at 12,000 rpm for 15 min at 4° C., supernatants collected and used for the cytokine multiplex bead-based kit (Bio-Rad Laboratories Inc., Hercules, Calif.). Proteins assayed included KC, macrophage inflammatory protein-1α (MIP-1α), RANTES, tumor necrosis factor-α (TNF-α), interleukin-1α (IL-1α), IL-1β, IL-2, IL-3, IL-4, IL-5, IL-6, IL-10, granulocyte monocyte colony stimulating factor (GM-CSF), granulocyte colony stimulating factor (G-CSF), interferon-γ (IFN-γ), IL-12 (p 40), IL-12 (p 70), IL-17. Cytokine assay plate layout consisted of eight standards in duplicate (32,000 to 1.95 pg/ml), two blank wells (for background fluorescence subtraction), and each sample in duplicate wells. The cytokine multiplex assay uses microbead and flow-based protein detection system (Bio-Plex Suspension Array System, Bio-Rad Laboratories Inc., Hercules, Calif.) based on the Luminex xMAP technology. In this quantitative assay, surfaces of fluorescence-coded microbeads were conjugated to specific antibodies directed against each cytokine or chemokine. Each fluorescence-coded microbead type was conjugated to one specific capture antibody, and consequently one specific target analyte. Each supernatant sample was first incubated with a mixture of all microbead types for 90 min at room temperature. Samples were then washed, incubated with a mixture of secondary biotinylated detection antibodies also directed against each target for 30 min at room temperature, washed again, and incubated with a streptavidin-coupled phycoerythrin reporter system for 10 min at room temperature. After a final wash, the samples were resuspended in buffer and subjected to flow cytometric analysis. The Bio-Plex system instrument uses fluidics, laser excitation, fluorescence detection, and digital signal processing for individual scanning and microbead identification. Each bead taken from the sample was identified based on its internal fluorescence signature, and the phycoerythrin reporter signal associated with that bead was quantified. The data was analyzed using Bio-Plex Manager™ 3.0 software (Bio-Rad).

ELISA for KC in Mice Urine and Serum, and Gro-α in Human Urine

All samples were thawed over ice. KC was determined in mice urine and serum using a Quantikine mouse KC kit (MKC00, R&D Systems, Minneapolis, Minn.) as per the manufacturer's instructions. The minimum detection limit for the KC assay is less than 2 pg/ml. Similarly, Gro-α was determined in human urine using a Quantikine human Gro-α kit (DGR00, R&D Systems, Minneapolis, Minn.) as per the manufacturer's instructions. The minimum detection limit for the Gro-α assay is less than 10 pg/ml. For both assays, each plate included eight standards, (1000 to 7.8 pg/ml), blank, and samples in duplicate.

Human Urine Measurements

After obtaining institutional IRB approval, urine samples from adult patients were analyzed on postoperative day two after living and deceased donor kidney transplants. The samples were collected and immediately placed on ice. The samples were centrifuged for 15 minutes at 3000 rpm at 4° C. The supernatant was decanted and stored at −80° C. until analysis. Kidney biopsies were performed one week post-transplant as clinically indicated for those considered having delayed (requiring dialysis) or slow improvement graft function.

Comparison, Quantification and Statistical Analysis of Data

All data involving animal experimentation was collected in a double-blind fashion. Sigma Stat 8.0, Sigma Plot 8.0 and MS Excel software were used for the statistical analysis and data presentation. The experimental data is expressed as mean±SEM. Statistical analysis included one-way ANOVA with appropriate post hoc analysis to test differences between means of various groups, and $p<0.05$ was considered to be statistically significant.

Example 2

There is significant data that early inflammatory changes underlie the pathogenesis of renal IRI (3; 8; 11; 15; 21). We therefore used a mouse model of renal IRI to examine kidney, blood and urine for evidence of changes in cytokine and chemokine expression using a protein array adapted to small volume samples. The earliest and most striking change was an increase in keratinocyte-derived chemokine (KC), a CXC chemokine that is structurally homologous to rat cytokine-induced neutrophil chemoattractant (CINC) and human growth-related oncogene-alpha (Gro-α) (19). KC levels were elevated in serum within one hour of renal ischemia in the mouse, and increased in kidney tissue and urine within three hours. To begin to evaluate the clinical significance, we examined humans with ischemic injury following a renal transplant and found a correlation of urine Gro-α levels with kidney injury that required dialysis. These studies provide evidence that KC and its human analogue, Gro-α, could be a valuable biomarker for early diagnosis and prognosis of acute renal failure.

Serum Creatinine and Kidney Histology in Mice after IRI

Figure 1:
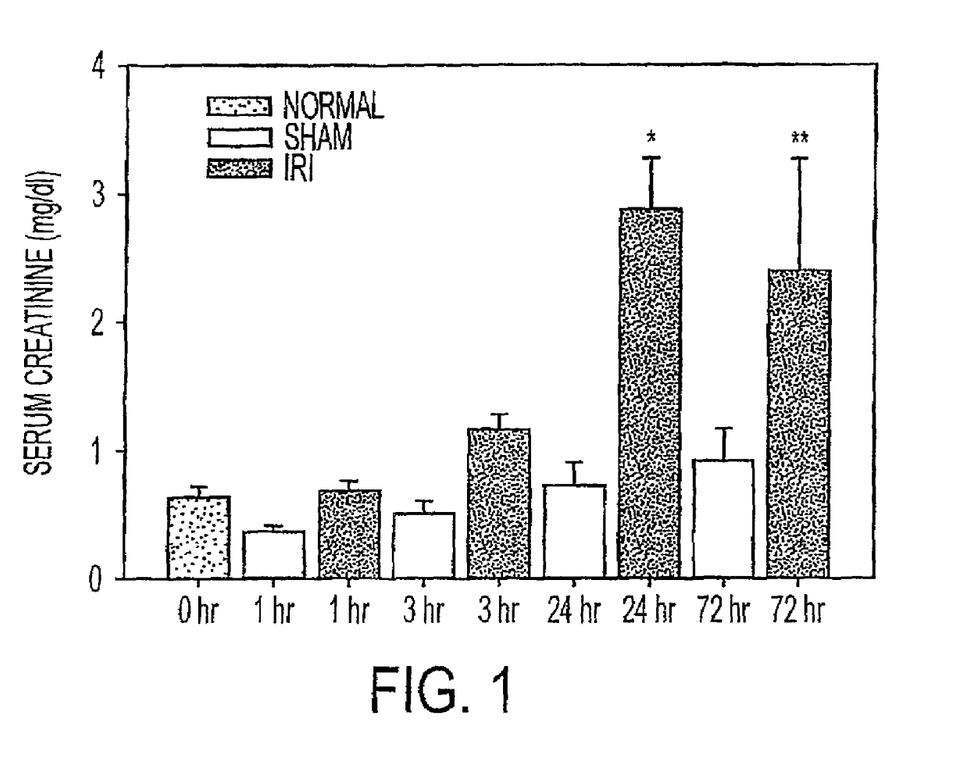
FIG. 1 shows a delayed rise in serum creatinine after renal IRI. Serum creatinine in normal mice (0 h—no surgery), and mice that underwent IRI or sham surgery and sacrificed at 1, 3, 24, and 72 h after surgery, n=10 per group. (*24 h IRI significantly higher than all groups except 72 h IRI; **72 h IRI significantly higher than all groups except 24 h IRI, $P<0.05$).
Figure 2A:
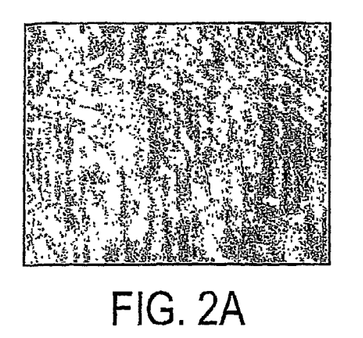
Figure 2B:
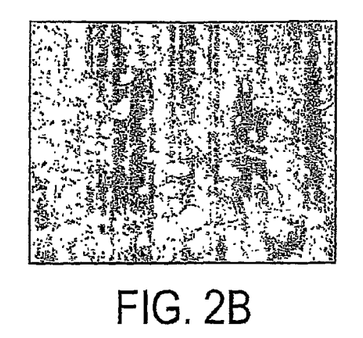
Figure 2C:
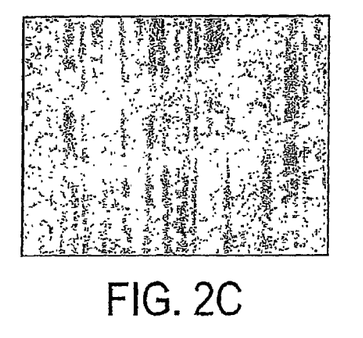
Figure 2D:
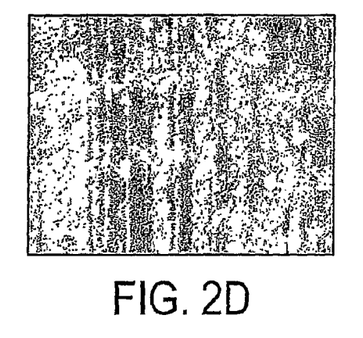
Figure 2E:
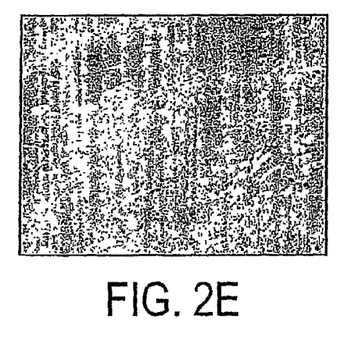
Figure 2F:
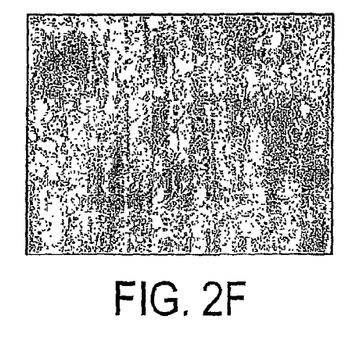
Figure 2G:
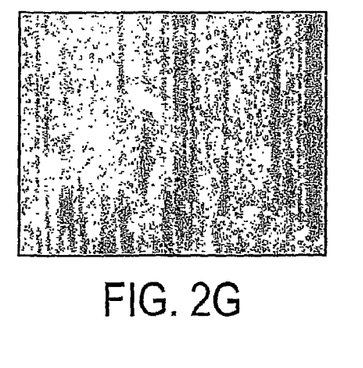
Figure 2H:
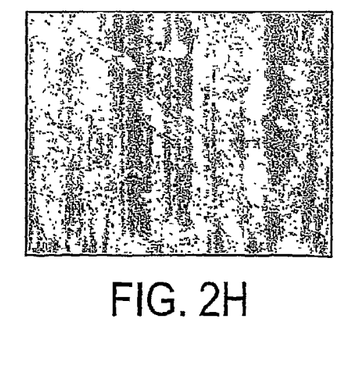
Figure 3A:
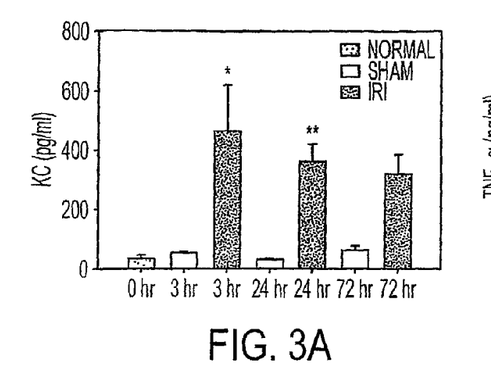
Figure 3B:
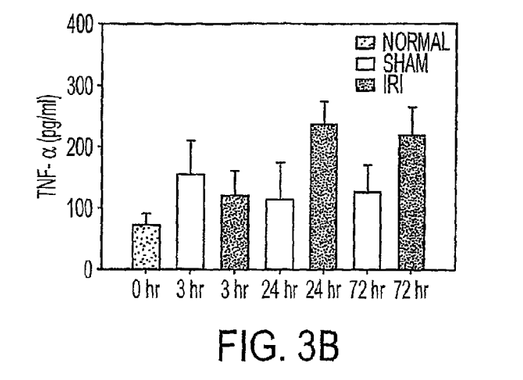
Figure 3C:
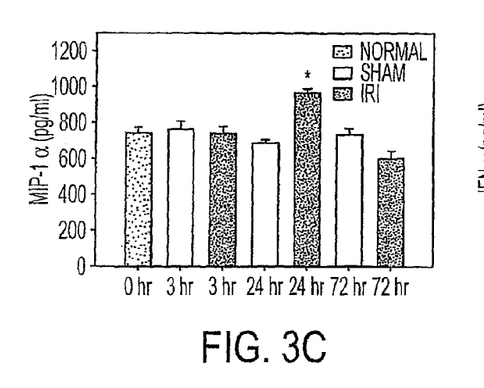
Figure 3D:
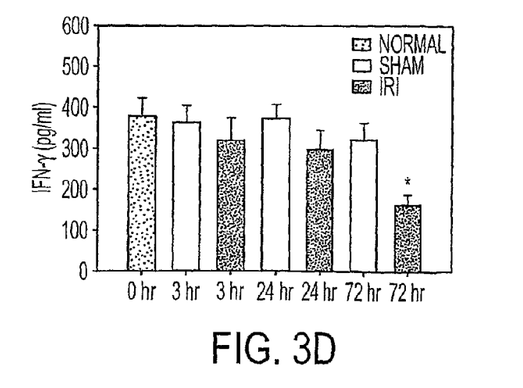
Figure 4A:
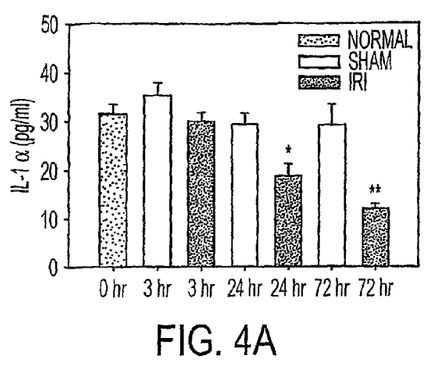
Figure 4B:
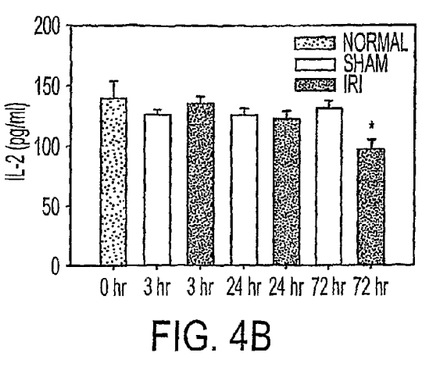
Figure 4C:
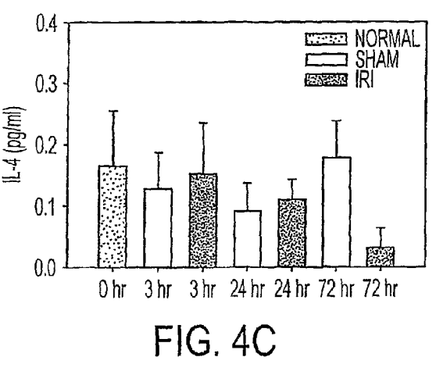
Figure 4D:
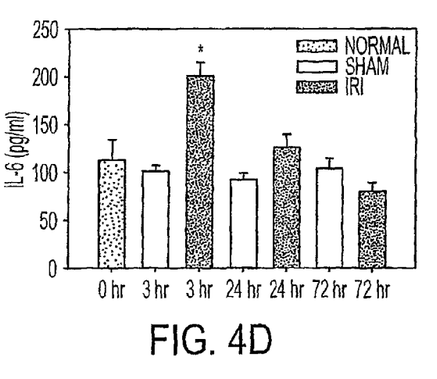
Figure 4E:
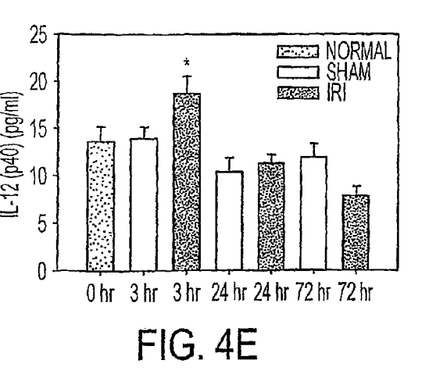
Figure 4F:
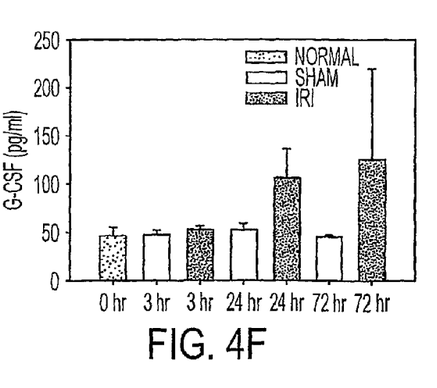

We evaluated serum creatinine (Cr) at various times following renal ischemia to define the severity and timing of renal failure in our model in order to correlate this with changes in potential biomarkers (FIG. 1). Compared to baseline values (0.64±0.86; n=10), Cr was significantly increased in mice 24 h (2.88±0.4; n=10) and 72 h (2.4±0.87; n=10) after ischemia. Kidney histology evaluated at intervals post-ischemia revealed that even by 1 h postischemia, red blood cell congestion and slight cast formation at the outer medulla were present compared to sham-operated animals. Furthermore the cytoplasm of some tubular epithelial cells was condensed and the endothelium was slightly edematous (FIG. 2C). At 3 h postischemia the histologic changes were more pronounced, with increased erythrocyte sludging in capillaries, condensation of tubular epithelium cytoplasm, epithelial cell necrosis, swelling of endothelial cells with basal membrane widening, and moderate cast formation (FIG. 2E). At 24 and 72 h postischemia there was significant tubular injury, characterized by extensive tubular necrosis and cast formation. Endothelial cells were markedly edematous, basal membranes were widened immensely, and capillaries were filled with erythrocytes (FIG. 2 G,I).

Example 3

Cytokines and Chemokines in Murine Renal Tissue

We utilized a cytokine multiplex assay to determine protein levels of 18 cytokines/chemokines in kidney tissue from normal (no surgery), and sham-operated (surgery but no renal artery clamping) or IRI mice at intervals after surgery. KC levels in ischemic kidney tissues were significantly increased 3 h postischemia compared to normal and sham groups ($P<0.05$) (FIG. 3). There were also significant early increase in IL-6 and IL-12(p40) at 3 hours after ischemia in IRI mice compared to sham operated mice (FIG. 4). TNF α showed a trend to increase with time post-ischemia. Meanwhile, IL-1α, IL-2, IL-4 and IFN-g showed significantly decreased/decline trend during time course in IRI mice when compared to sham group. MIP-1α was significantly higher 24 h after IRI compared to all groups ($P<0.05$). No differences were noted across groups for levels of IL-1β, IL-3, IL-5, IL-10, IL-12 (p70), IL-17, GM-CSF and RANTES (data not shown).

Example 4

KC in Mice Serum

Figure 5:
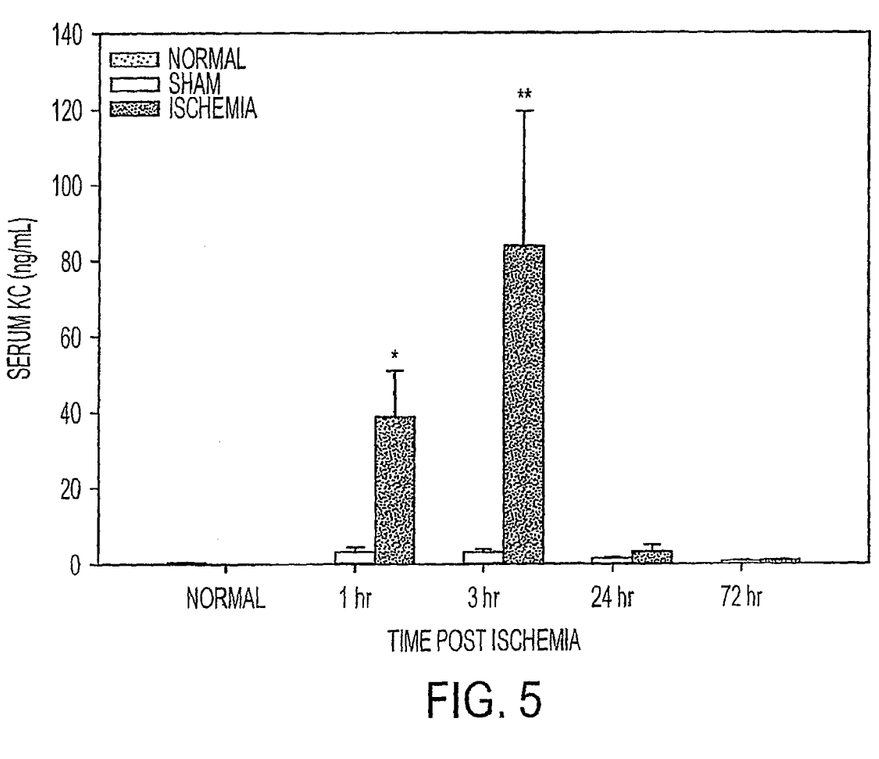
FIG. 5 shows elevated serum KC early after renal IRI. KC levels in serum from normal mice (0 h—no surgery), and mice that underwent IRI or sham surgery and sacrificed at 1, 3, 24, and 72 h after surgery. (*, $P<0.003$, **, $P<0.0004$ vs. sham group. n=5-12 per group)

After identifying an increase in KC with the multiplex assay, we measured KC levels in serum taken from normal, sham-surgery or IRI mice using an ELISA assay. Compared to normal or sham-operated mice, KC levels in serum were significantly elevated at 1 and 3 h postischemia, and dropped to baseline levels by 24 h (FIG. 5).

Example 5

KC in Mice Urine

Figure 6:
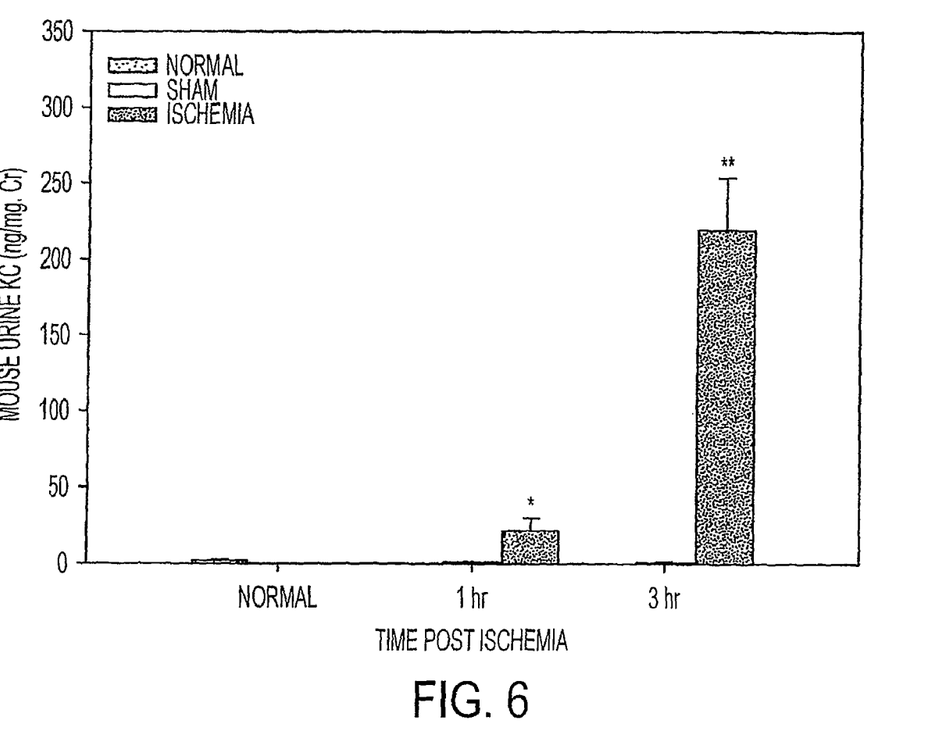
FIG. 6 shows increased urine KC early after IRI. KC in urine from normal mice (0 h—no surgery), and mice that underwent IRI or sham surgery and sacrificed at 1 and 3 h after surgery. (*, $P<0.02$, **, $P<0.0001$; n=8 per group)

To examine if urine KC could be a useful noninvasive marker of renal IRI, we measured KC in urine from normal mice, as well as at early time points in urine from sham surgery or IRI mice. Urine KC levels were comparable in normal, sham and ischemic mice at 1 h IRI, however they were significantly increased at 3 h post-ischemia in ischemic mice when compared to sham operated mice (FIG. 6).

Example 6

Gro-α in Human Urine During Renal IRI

Figure 7:
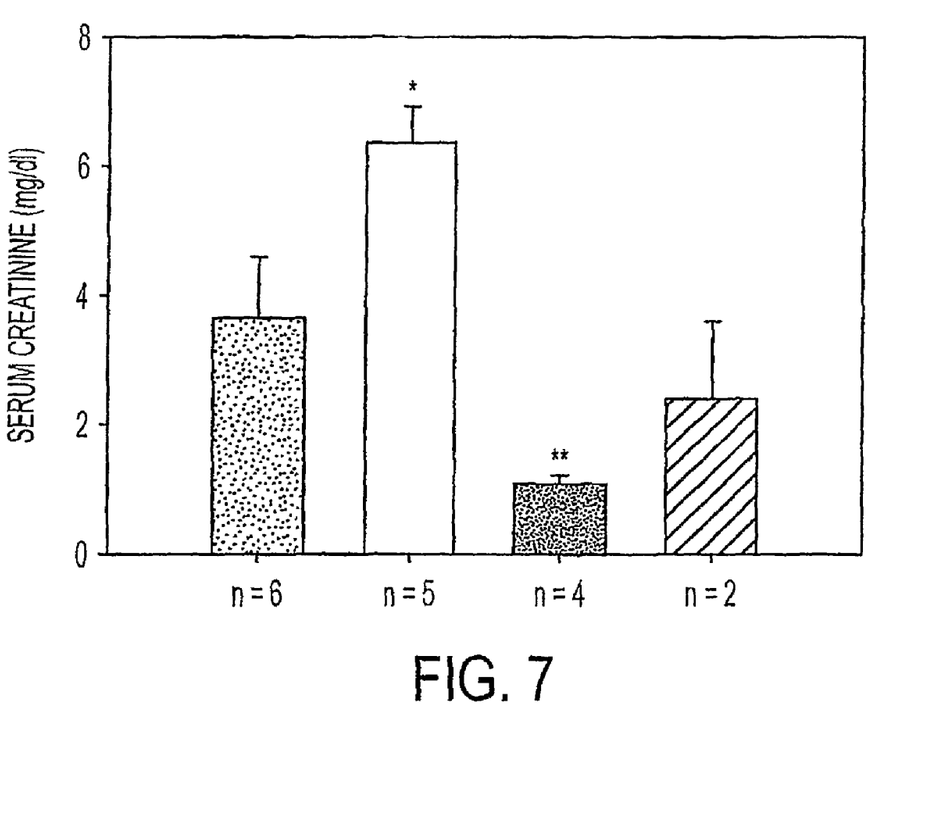
FIG. 7 shows elevated day 2 serum creatinines in humans with deceased donor kidney transplants compared to those with live donor kidney transplants. Groups include patients who received deceased donor kidneys with (☐) prompt or (☐) delayed graft function, or live donor kidneys with (■) prompt or (▨) slow graft function. *Deceased kidney recipients with delayed graft function have significantly higher serum creatinines than living kidney recipients with slow graft function; **Living kidney recipients with prompt graft function have significantly lower serum creatinines than all groups.
Figure 8:
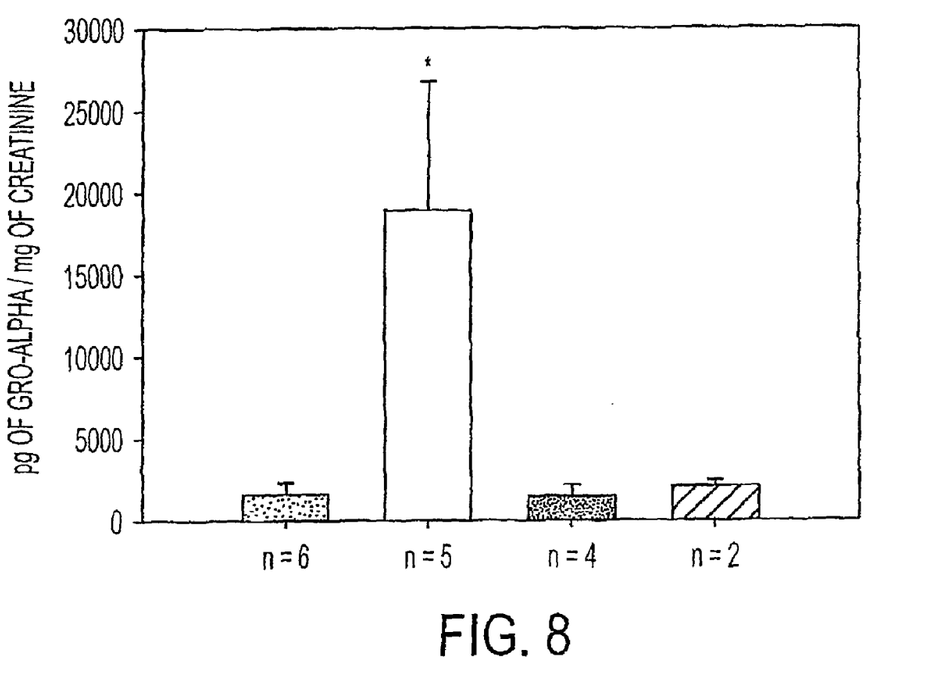
FIG. 8 shows elevated day 2 urine Gro-α patients with deceased donor kidney allografts and delayed graft function. Groups include patients who received deceased donor kidneys with (☐) prompt or (☐) delayed graft function, or live donor kidneys with (■) prompt or (▨) slow graft function. * Deceased kidney recipients with delayed graft function have significantly higher Gro-α than deceased with prompt function and living with slow graft function.

A major goal of this work is to identify pathways or markers using controlled models that have future relevance to human ischemic renal injury. To examine if the elevation in urine KC in mice with renal IRI were translatable to humans, we hypothesized that the human analogue of KC, Gro-α, correlates with acute kidney injury in patients with during kidney transplantation. We performed a pilot study in patients after kidney transplantation measuring day 2 urine after they had come out of the ICU. Recipients of deceased donor kidneys had higher SCr than those with live donor kidneys on day 2 after transplantation (FIG. 7). Of the four groups represented in FIG. 7 only patients who received deceased donor kidneys progressed to requiring short term dialysis until resolution of the ARF. This group had significantly higher urine Gro-α levels than did the groups who received deceased or live donor kidneys with good graft function (FIG. 8). Those with elevated day 2 urine Gro-α levels also had evidence of ATN on the day 7-10 biopsies (data not shown). Three of the five recipients of deceased donor kidneys with delayed graft function had biopsies: two had focal ATN with isometric vacuolization, and one had moderate ATN and acute antibody-mediated rejection. Renal biopsy from only one out of the six patients who received deceased donor kidneys with prompt graft function showed severe ATN with isometric vacuolization. From the recipients of live donors, one of the four had prompt graft function initially but then deteriorated, and was found to have mild focal ATN. Of the 2 patients with live donor kidneys with slow graft function (suboptimal improvement in graft function but not serious enough to require dialysis), one had mild acute tubular injury with focal interstitial hemorrhage, and one had severe acute cellular rejection with arteritis.

Example 7

KC in Lung Tissue After Renal IRI

Distant organ injury, particularly to lung, contributes to the high mortality associated with acute renal failure (ARF). ARF has been demonstrated to directly cause pulmonary cellular inflammation, increased albumin permeability, disregulation of salt and water transporters, and changes in heat shock proteins. The mechanisms underlying the distant organ effects of ARF are largely unknown. Given the known inflammatory pathogenesis of acute lung injury and adult respiratory distress syndrome (ARDS), we hypothesized that early inflammatory responses in lung could underlie many of the lung changes during ARF. We used a multiplex protein-array technique to study lung expression of 18 cytokines and chemokines: KC, MIP-1, RANTES, TNF-, IL-1, IL-1, IL-2, IL-3, IL-4, IL-5, IL-6, IL-10, GM-CSF, G-CSF, IFN-, IL-12 (p 40), IL-12 (p 70), IL-17 in a mouse model of ischemic ARF. The earliest and most consistent protein that rose in lung was KC, with 3 hr post-kidney ischemia values approximately 40- and 2-fold greater than normal and sham animals, respectively. Lung IL-6 protein also rose 4- and 1.5-fold greater than normal and sham animals 3 hrs after kidney ischemia. Both lung KC and IL-6 levels decreased at 24 hr compared to 3 hr levels. Conventional ELISA validated the protein array data. To test if the increase in lung KC lung levels were localized, we performed immunohistochemical staining of inflation-fixed lung in sham and ARF animals 24 hrs after ischemia. A marked upregulation of KC protein was found in both airways and blood vessels in the ARF group, which was minimal in sham-operated animals. These data demonstrate that acute kidney ischemia leads to rapid rise lung KC. A significant, but reduced rise in lung KC occurs with sham surgery alone. Given that KC is an important chemokine in the recruitment of neutrophils and macrophages to sites of injury, we propose that early upregulation of lung KC after kidney injury is an important mediator of distant lung inflammation. Identifying and targeting mediators of distant organ injury during ARF should reduce the high mortality associated with ARF.

Mice that underwent IRI or sham surgery were sacrificed at 3, 24, and 72 hours after surgery. Ten mice were used in each group. At 3 hours the IRI mice had significantly higher KC than all other groups. At 3 hours the sham surgery group had significantly higher KC than the no surgery and the 72 hour sham surgery.

Animals

Male C57BL/6 mice were obtained from The Jackson Laboratory (Bar Harbor, Me.) and housed under pathogen-free conditions, according to NIH guidelines.

Surgical Procedures

An established model of renal IRI Was used (12). Briefly, mice weighing 25-30 gm were anesthetized with an i.p. injection of sodium pentobarbital (75 mg/kg). Bilateral flank incisions were made, and the kidneys were exposed. Following abdominal incisions, renal pedicles were bluntly dissected and a nontraumatic vascular clamp was applied across each of the pedicles for 30 min. Animals were sacrificed at 1, 3, 24, and 72 hr after surgery.

Protein Array for Cytokines in Kidney Tissue from Mice

Total Protein Analysis

Kidney samples were thawed over ice. Part of each kidney was homogenized in T-PER Tissue Protein Extraction Reagent (Pierce, Rockford, Ill.). The homogenate was centrifuged at 10,000 rpm for 5 min at 4° C. The supernatant was collected to determine total protein concentration using a micro BCA protein assay kit (Pierce, Rockford, Ill.).

Cytokine Analysis

Weighed kidney samples containing 500 μg/ml protein per sample were homogenized with cell lysis buffer (Cell Lysis Kit, Bio-Rad Laboratories Inc., Hercules, Calif.). Tissue homogenates were centrifuged at 12,000 rpm for 15 min at 4° C., supernatants collected and used for the cytokine multiplex bead-based kit (Bio-Rad Laboratories Inc., Hercules, Calif.). Proteins assayed included KC, macrophage inflammatory protein-1α (MIP-1α), RANTES, tumor necrosis factor-α (TNF-α), interleukin-1α (IL-1a), IL-1β, IL-2, IL-3, IL-4, IL-5, IL-6, IL-10, granulocyte monocyte colony stimulating factor (GM-CSF), granulocyte colony stimulating factor (G-CSF), interferon-γ (IFN-g), IL-12 (p 40), IL-12 (p 70), IL-17. The data was analyzed using Bio-Plex Manager™ 3.0 software (Bio-Rad).

ELISA for KC in Mice Urine and Serum

All samples were thawed over ice. KC was determined in mice urine and serum using a Quantikine mouse KC kit (MKC00, R&D Systems, Minneapolis, Minn.) as per the manufacturer's instructions.

Comparison, Quantification and Statistical Analysis of Data

All data involving animal experimentation was collected in a double-blind fashion. Sigma Stat 8.0, Sigma Plot 8.0 and MS Excel software were used for the statistical analysis and data presentation. The experimental data is expressed as mean±SEM. $P<0.05$ was considered to be statistically significant.

REFERENCES

The disclosure of each reference cited is expressly incorporated herein.

1. Bonventre, J. and Rabb, H. Biomarkers group: acute renal failure retreat. American Society of Nephrology Research Report. *J Am Soc Nephrol* 16: 1886-1903, 2005.
2. Daemen M A, de Vries B, van't Veer C, Wolfs T G and Buurman W A. Apoptosis and chemokine induction after renal ischemia-reperfusion. *Transplantation* 71: 1007-1011, 2001.
3. Goes N, Urmson J, Ramassar V and Halloran P F. Ischemic acute tubular necrosis induces an extensive local cytokine response. Evidence for induction of interferon-gamma, transforming growth factor-beta 1, granulocyte-macrophage colony-stimulating factor, interleukin-2, and interleukin-10. *Transplantation* 59: 565-572, 1995.
4. Hewitt S M, Dear J and Star R A. Discovery of protein biomarkers for renal diseases. *J Am Soc Nephrol* 15: 1677-1689, 2004.
5. Humes H D. Acute renal failure: prevailing challenges and prospects for the future. *Kidney Int* 50: S26-S32, 1995.
6. Ichimura T, Hung C C, Yang S A, Stevens J L and Bonventre J V. Kidney injury molecule-1: a tissue and urinary biomarker for nephrotoxicant-induced renal injury. *Am J Physiol Renal Physiol* 286: F552-F563, 2004.
7. Kwon O, Molitoris B A, Pescovitz M and Kelly K J. Urinary actin, interleukin-6, and interleukin-8 may predict sustained ARF after ischemic injury in renal allografts. *Am J Kidney Dis* 41: 1074-1087, 2003.
8. Lemay S, Rabb H, Postler G and Singh A K. Prominent and sustained up-regulation of gp130-signaling cytokines and the chemokine MIP-2 in murine renal ischemia-reperfusion injury. *Transplantation* 69: 959-963, 2000.
9. Liehn E A, Schober A, Weber C. Blockade of keratinocyte-derived chemokine inhibits endothelial recovery and enhances plaque formation after arterial injury in ApoE-deficient mice. *Arterioscler Thromb Vasc Biol*. 24:1891-6, 2004.
10. Mishra J, Dent C, Tarabishi R, Mitsnefes M M, Ma Q, Kelly C, Ruff S M, Zahedi K, Shao M, Bean J, Mori K, Barasch J and Devarajan P. Neutrophil gelatinase-associated lipocalin (NGAL) as a biomarker for acute renal injury after cardiac surgery. *Lancet* 365: 1231-1238, 2005.
11. Miura M, Fu X, Zhang Q W, Remick D G and Fairchild R L. Neutralization of Gro alpha and macrophage inflammatory protein-2 attenuates renal ischemia/reperfusion injury. *Am J Pathol* 159: 2137-2145, 2001.
12. Parikh C R, Jani A, Melnikov V Y, Faubel S and Edelstein C L. Urinary interleukin-18 is a marker of human acute tubular necrosis. *Am J Kidney Dis* 43: 405-414, 2004.
13. Rabb H. Novel urinary markers for early diagnosis of ARF. *Am J Kidney Dis* 42: 599-600, 2003.
14. Rabb H, Daniels F, O'Donnell M, Haq M, Saba S R, Keane W and Tang W W. Pathophysiological role of T lymphocytes in renal ischemia-reperfusion injury in mice. *Am J Physiol Renal Physiol* 279: F525-F531, 2000.

15. Rice J C, Spence J S, Yetman D L and Safirstein R L. Monocyte chemoattractant protein-1 expression correlates with monocyte infiltration in the post-ischemic kidney. *Ren Fail* 24: 703-723, 2002.
16. Safirstein R, Megyesi J, Saggi S J, Price P M, Poon M, Rollins B J and Taubman M B. Expression of cytokine-like genes JE and KC is increased during renal ischemia. *Am J Physiol* 261: F1095-F1101, 1991.
17. Star R A. Treatment of acute renal failure. *Kidney Int* 54: 1817-1831, 1998.
18. Thomas M J, Smith A, Head D H, Milne L, Nicholls A, Pearce W, Vanhaesebroeck B, Wymann M P, Hirsch E, Trifilieff A, Walker C, Finan P, Westwick J. Airway inflammation: chemokine-induced neutrophilia and the calass I phosphoinositide 3-kinases. *Eur J Immunol* 351283-91
19. Walz A, Kunkel S L and Strieter R M. C-X-C Chemokines—an overview. In: Chemokines in Disease, edited by Koch A E and Strieter R M. Austin: R.G. Landes Company, 1996, p. 1-25.
20. Westhuyzen J, Endre Z H, Reece G, Reith D M, Saltissi D and Morgan T J. Measurement of tubular enzymuria facilitates early detection of acute renal impairment in the intensive care unit. *Nephrol Dial Transplant* 18: 543-551, 2003.
21. Zhang Y, Woodward V K, Shelton J M, Richardson J A, Zhou X J, Link D, Kielar M L, Jeyarajah D R and Lu C Y. Ischemia-reperfusion induces G-CSF gene expression by renal medullary thick ascending limb cells in vivo and in vitro. *Am J Physiol Renal Physiol* 286: F1193-F1201, 2004.

I claim:

1. A method for detecting acute kidney injury (AKI) comprising:
   determining a first amount of Gro-alpha in urine, serum, or tissue of a human patient;
   comparing the determined first amount for the patient to a second amount determined for control patients with healthy kidneys;
   assigning the patient to a first group if the first amount is elevated relative to the second amount determined for control patients and assigning the patient to a second group if the first amount is not elevated relative to the second amount determined for control patients, wherein the first group is identified as having acute kidney injury.

2. The method of claim 1 further comprising:
   providing a diagnosis of acute kidney injury if the patient is in the first group.

3. The method of claim 1 further comprising:
   predicting that the patient will need dialysis if the patient is in the first group.

4. The method of claim 1 further comprising:
   recommending dialysis for the patient if the patient is in the first group.

5. The method of claim 1 further comprising:
   testing a drug on patients in the first and second group; and
   comparing drug efficacy in the first group to drug efficacy in the second group.

6. The method of claim 1 further comprising:
   testing a therapeutic regimen on patients in the first and second group; and
   comparing therapeutic efficacy in the first group to drug efficacy in the second group.

7. The method of claim 1 further comprising:
   prescribing a drug or therapy to the patient if the patient is in the first group.

8. The method of claim 1 wherein the patient is assigned to the first group if the first amount determined is at least two-fold higher than the second amount.

9. The method of claim 1 wherein the patient is assigned to the first group if the first amount determined is at least three-fold higher than the second amount.

10. The method of claim 1 wherein the patient is assigned to the first group if the first amount determined is at least four-fold higher than the second amount.

11. The method of claim 1 wherein the patient is assigned to the first group if the first amount determined is at least five-fold higher than the second amount.

12. The method of claim 1 wherein the first amount is determined in urine.

13. The method of claim 1 wherein the first amount is determined in serum.

14. The method of claim 1 wherein the first amount is determined in tissue.

15. The method of claim 12 wherein the first amount is normalized to an amount of creatinine present in the urine.

16. The method of claim 12 wherein the first amount is at least 5,000 pg/mg of creatinine in the urine.

17. The method of claim 12 wherein the first amount is at least 10,000 pg/mg of creatinine in the urine.

18. The method of claim 12 wherein the first amount is at least 15,000 pg/mg of creatinine in the urine.

19. The method of claim 12 wherein the first amount is at least 20,000 pg/mg of creatinine in the urine.

20. The method of claim 13 wherein the first amount is at least 15,000 pg/ml of serum.

21. The method of claim 13 wherein the first amount is at least 20,000 pg/ml of serum.

22. The method of claim 14 wherein the first amount is at least 100 pg/mg.

23. The method of claim 14 wherein the first amount is at least 200 pg/mg.

24. The method of claim 14 wherein the first amount is at least 300 pg/mg.

25. The method of claim 14 wherein the first amount is at least 400 pg/mg.

26. The method of claim 1 wherein the step of determining is performed prior to a rise in serum creatinine levels in the patient.

27. The method of claim 1 wherein the patient is a kidney transplant recipient.

28. The method of claim 27 wherein the kidney transplant is from a deceased donor.

29. The method of claim 27 wherein the kidney transplant if from a live donor.

30. The method of claim 1 wherein the patient is before, during, or after heart surgery.

31. The method of claim 30 wherein the patient is within 7 days of heart surgery.

32. The method of claim 30 wherein the patient is within the first 12 hours post surgery.

33. The method of claim 30 wherein the patient is within the first 6 hours post-surgery.

34. The method of claim 30 wherein the patient is within the first 3 hours post-surgery.

35. The method of claim 1 wherein the patient is in an intensive care unit.

36. The method of claim 1 wherein the first amount of Gro-alpha is determined with an antibody which specifically binds to Gro-alpha.

37. The method of claim 36 wherein the antibody is immobilized to a solid support.

38. The method of claim 37 wherein the antibody is immobilized in an array of antibodies.

39. The method of claim 1 wherein the patient has been exposed to a toxin.

40. The method of claim 1 wherein the patient is at risk of sepsis.

41. The method of claim 1 wherein the patient is in shock.

42. The method of claim 1 further comprising:
   predicting a higher risk of morbidity and/or mortality if the patient is assigned to the first group.

43. A method for detecting acute kidney injury (AKI) comprising:
   determining a first amount of Gro-alpha mRNA in urine, serum, or tissue of a human patient;
   comparing the determined first amount for the patient to a second amount determined for control patients with healthy kidneys;
   assigning the patient to a first group if the first amount is elevated relative to the second amount determined for control patients and assigning the patient to a second group if the first amount is not elevated relative to the second amount determined for control patients, wherein the first group is identified as having acute kidney injury.

44. A method of reducing lung damage associated with acute kidney injury, comprising:
   administering to a human patient suspected of having acute kidney injury an antibody which specifically binds to human Gro-alpha, whereby risk of mortality is reduced.

45. The method of claim 44 wherein the antibody is administered systemically.

46. The method of claim 44 wherein the antibody is administered directly to the lungs.

47. The method of claim 44 wherein urine, serum or tissue of the patient has been tested for amount of Gro-alpha and said amount has been found to be elevated relative to healthy controls.

48. The method of claim 44 wherein the patient has undergone heart surgery.

49. The method of claim 44 wherein the patient has sepsis.

50. The method of claim 44 wherein the patient is in shock.

51. The method of claim 44 wherein the patient has been exposed to a toxin.

* * * * *

SEQUENCE LISTING

```
<160> NUMBER OF SEQ ID NOS: 2

<210> SEQ ID NO 1
<211> LENGTH: 107
<212> TYPE: PRT
<213> ORGANISM: Homo sapiens

<400> SEQUENCE: 1

Met Ala Arg Ala Ala Leu Ser Ala Ala Pro Ser Asn Pro Arg Leu Leu
 1               5                  10                  15

Arg Val Ala Leu Leu Leu Leu Leu Val Ala Ala Gly Arg Arg Ala
                20                  25                  30

Ala Gly Ala Ser Val Ala Thr Glu Leu Arg Cys Gln Cys Leu Gln Thr
            35                  40                  45

Leu Gln Gly Ile His Pro Lys Asn Ile Gln Ser Val Asn Val Lys Ser
        50                  55                  60

Pro Gly Pro His Cys Ala Gln Thr Glu Val Ile Ala Thr Leu Lys Asn
65                  70                  75                  80

Gly Arg Lys Ala Cys Leu Asn Pro Ala Ser Pro Ile Val Lys Lys Ile
                85                  90                  95

Ile Glu Lys Met Leu Asn Ser Asp Lys Ser Asn
                100                 105

<210> SEQ ID NO 2
<211> LENGTH: 1103
<212> TYPE: DNA
<213> ORGANISM: Homo sapiens

<400> SEQUENCE: 2
cacagagccc gggccgcagg cacctcctcg ccagctcttc cgctcctctc acagccgcca      60
gacccgcctg ctgagcccca tggcccgcgc tgctctctcc gccgccccca gcaatccccg     120
gctcctgcga gtggcactgc tgctcctgct cctggtagcc gctggccggc gcgcagcagg     180
agcgtccgtg gccactgaac tgcgctgcca gtgcttgcag accctgcagg gaattcaccc     240
caagaacatc caaagtgtga acgtgaagtc ccccggaccc cactgcgccc aaaccgaagt     300
catagccaca ctcaagaatg gcggaaagc ttgcctcaat cctgcatccc ccatagttaa     360
gaaaatcatc gaaagatgc tgaacagtga caaatccaac tgaccagaag ggaggaggaa     420
gctcactggt ggctgttcct gaaggaggcc ctgcccttat aggaacagaa gaggaaagag     480
agacacagct gcagaggcca cctggattgt gcctaatgtg tttgagcatc gcttaggaga     540
```

-continued

| | | | | | |
|---|---|---|---|---|---|
| agtcttctat | ttatttattt | attcattagt | tttgaagatt | ctatgttaat | attttaggtg | 600 |
| taaaataatt | aagggtatga | ttaactctac | ctgcacactg | tcctattata | ttcattcttt | 660 |
| ttgaaatgtc | aaccccaagt | tagttcaatc | tggattcata | tttaatttga | aggtagaatg | 720 |
| ttttcaaatg | ttctccagtc | attatgttaa | tatttctgag | gagcctgcaa | catgccagcc | 780 |
| actgtgatag | aggctggcgg | atccaagcaa | atggccaatg | agatcattgt | gaaggcaggg | 840 |
| gaatgtatgt | gcacatctgt | tttgtaactg | tttagatgaa | tgtcagttgt | tatttattga | 900 |
| aatgatttca | cagtgtgtgg | tcaacatttc | tcatgttgaa | actttaagaa | ctaaaatgtt | 960 |
| ctaaatatcc | cttggacatt | ttatgtcttt | cttgtaaggc | atactgcctt | gtttaatggt | 1020 |
| agttttacag | tgtttctggc | ttagaacaaa | ggggcttaat | tattgatgtt | ttcatagaga | 1080 |
| atataaaaat | aaagcactta | tag | | | | 1103 |